(12) United States Patent
DeCarlo

(10) Patent No.: US 9,031,668 B2
(45) Date of Patent: May 12, 2015

(54) VENTED POSITIONER AND SPACER AND METHOD OF USE

(75) Inventor: Arnold V. DeCarlo, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1368 days.

(21) Appl. No.: 12/536,616

(22) Filed: Aug. 6, 2009

(65) Prior Publication Data
US 2011/0034919 A1 Feb. 10, 2011

(51) Int. Cl.
*A61B 18/18* (2006.01)
*A61B 17/34* (2006.01)

(52) U.S. Cl.
CPC ............. *A61B 17/3403* (2013.01); *A61B 18/18* (2013.01); *A61B 2017/3407* (2013.01); *A61B 2017/3411* (2013.01); *A61B 2018/1869* (2013.01)

(58) Field of Classification Search
CPC ................... A61B 17/3403; A61B 2017/3407; A61B 2017/3411; A61B 2018/1869; A61B 18/18; A61B 18/1815
USPC ........... 606/129, 130, 108, 144–148, 185, 33, 606/41; 600/417, 429; 604/164.01, 174; 607/101
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,798,215 A | 1/1989 | Turner | |
| 5,097,844 A | 3/1992 | Turner | |
| 5,417,210 A | 5/1995 | Funda et al. | |
| 5,626,607 A | 5/1997 | Malecki et al. | |
| 5,749,549 A * | 5/1998 | Ashjaee ......................... 248/168 |
| 6,031,375 A | 2/2000 | Atalar et al. | |
| 6,117,143 A * | 9/2000 | Hynes et al. ................... 606/130 |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael Peffley
*Assistant Examiner* — Samantha Good

(57) ABSTRACT

Disclosed is a device positioner for guiding and positioning energy delivery devices during a surgical procedure. The energy delivery device positioner includes a body, a plurality of legs coupled to the body and a plurality of ribs connected to the body. The body includes a body facing surface and a plurality of device positioner apertures defined therein. The device positioner apertures are configured to receive an energy delivery device therethrough. The plurality of legs includes at least one foot extending beyond the patient facing surface of the body with the distal end of the foot configured to contact patient tissue and elevate the patient facing surface of the body such that the patient facing surface is spaced away from patient tissue. The plurality of ribs form one or more air flow aperture.

10 Claims, 5 Drawing Sheets

(56) References Cited

U.S. PATENT DOCUMENTS

| | | |
|---|---|---|
| 6,241,725 B1 | 6/2001 | Cosman |
| 6,267,770 B1 | 7/2001 | Truwit |
| 6,355,033 B1 | 3/2002 | Moorman et al. |
| 6,375,606 B1 | 4/2002 | Garibaldi et al. |
| 6,451,015 B1 | 9/2002 | Rittman, III et al. |
| 6,564,806 B1 | 5/2003 | Fogarty et al. |
| 6,603,994 B2 | 8/2003 | Wallace et al. |
| 6,652,520 B2 | 11/2003 | Moorman et al. |
| 6,725,080 B2 | 4/2004 | Melkent et al. |
| 7,197,363 B2 | 3/2007 | Prakash et al. |
| 7,226,446 B1 | 6/2007 | Mody et al. |
| 7,278,991 B2 | 10/2007 | Morris et al. |
| 7,282,049 B2 | 10/2007 | Orszulak et al. |
| 7,422,586 B2 | 9/2008 | Morris et al. |
| 7,439,736 B2 | 10/2008 | Meaney et al. |
| 7,467,015 B2 | 12/2008 | Van der Weide |
| 7,565,207 B2 | 7/2009 | Turner et al. |
| 7,642,451 B2 | 1/2010 | Bonn |
| 7,875,024 B2 | 1/2011 | Turovskiy et al. |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |
| 8,216,227 B2 | 7/2012 | Podhajsky |
| 8,221,418 B2 | 7/2012 | Prakash et al. |
| 2002/0022836 A1 | 2/2002 | Goble et al. |
| 2002/0120261 A1 | 8/2002 | Morris et al. |
| 2004/0039429 A1 | 2/2004 | Daniel et al. |
| 2004/0097805 A1 | 5/2004 | Verard et al. |
| 2004/0242992 A1 | 12/2004 | Hareyama |
| 2004/0267256 A1 | 12/2004 | Garabedian et al. |
| 2005/0137662 A1 | 6/2005 | Morris et al. |
| 2006/0079887 A1 | 4/2006 | Buysse et al. |
| 2006/0122581 A1 | 6/2006 | Ein-Gal |
| 2006/0142757 A1 | 6/2006 | Daniel et al. |
| 2007/0106305 A1* | 5/2007 | Kao et al. ............ 606/130 |
| 2007/0203480 A1 | 8/2007 | Mody et al. |
| 2008/0021448 A1 | 1/2008 | Orszulak et al. |
| 2008/0255582 A1* | 10/2008 | Harris ............ 606/129 |
| 2009/0138005 A1 | 5/2009 | Prakash et al. |
| 2009/0171203 A1 | 7/2009 | Avital et al. |
| 2009/0187180 A1 | 7/2009 | Brannan |
| 2009/0192510 A1 | 7/2009 | Bahney |
| 2009/0198226 A1 | 8/2009 | Prakash et al. |
| 2009/0198227 A1 | 8/2009 | Prakash |
| 2009/0222002 A1 | 9/2009 | Bonn et al. |
| 2009/0248005 A1 | 10/2009 | Rusin et al. |
| 2009/0248006 A1 | 10/2009 | Paulus et al. |
| 2009/0264877 A1 | 10/2009 | DeCarlo |
| 2009/0264899 A1* | 10/2009 | Appenrodt et al. ............ 606/130 |
| 2009/0306652 A1 | 12/2009 | Buysse et al. |
| 2009/0326620 A1 | 12/2009 | Rossetto et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0053015 A1 | 3/2010 | Willyard |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286683 A1 | 11/2010 | Podhajsky |
| 2010/0305559 A1 | 12/2010 | Brannan et al. |
| 2010/0305560 A1 | 12/2010 | Peterson |
| 2010/0305561 A1 | 12/2010 | Prakash et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 070 518 | 1/2001 |
| EP | 1 159 926 | 5/2001 |
| EP | 1 186 274 | 3/2002 |
| EP | 1 278 007 | 1/2003 |
| EP | 1 645 234 | 4/2006 |
| EP | 1 645 235 | 4/2006 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |

(56) References Cited

FOREIGN PATENT DOCUMENTS

| JP | 11244298 | 9/1999 |
|---|---|---|
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO 99/04710 | 2/1999 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/009528 | 2/2005 |
| WO | WO2005/016119 | 2/2005 |

OTHER PUBLICATIONS

Anderson et al.. "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/Wire Localizer, Namic ® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington. D.C.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Dumey et al., "Antennas for Medical Applications", Antenna Handbook: Theory Application and Design, p. 24-40, Van Nostrand Reinhold. 1988 New York. V.T. Lo. S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94In Biologic Effects of Nonionizing Electromagnetic Fields, CRC Press, Inc., pp. 1424-1428.

Chung et al., "Clinical Experience of Sutureless Closed Hemorrhoidectomy with LigaSure™ " Diseases of the Colon & Rectum, vol. 46, No. 1, Jan. 2003.

Cosman et al., "Radiofrequency Lesion Generation and its Effect on Tissue Impedance", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Cosman et al., "Methods of Making Nervous System Lesions" In William RH, Rengachary SS (eds): Neurosurgery, New York: McGraw•Hill, vol. 111, (1984), pp. 2490-2499.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

(56) References Cited

OTHER PUBLICATIONS

LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica. vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite Element Codes to Model Electrical Heating and Non•Llnear Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated.Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.

(56) References Cited

OTHER PUBLICATIONS

European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University. Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.

* cited by examiner

VENTED POSITIONER AND SPACER AND METHOD OF USE

BACKGROUND

1. Technical Field

The present disclosure relates to apparatus, systems and methods for providing energy to biological tissue and, more particularly, to apparatuses, systems and methods for precise placement of energy delivery devices in a surgical procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated and a patient return electrode is placed remotely from the active electrode to carry the current back to the generator. In bipolar electrosurgery, the active and return electrodes are placed in close proximity to each other, e.g., at the surgical site, and electrosurgical currents are passed therebetween. In microwave electrosurgery, the antenna of the microwave energy delivery device generates electromagnetic fields in the adjacent tissue without the generation of electrosurgical currents between an active electrode and a return electrode as discussed hereinabove.

Radio frequency energy may be delivered to targeted tissue in an ablation procedure by electrosurgical probes or by an electrosurgical antenna. In the case of tissue ablation using electrosurgical probes, electrode pairs are positioned in the surgical site to delivery high frequency electrosurgical currents between the pairs of active (+) and return (−) electrodes. An active (+) electrode and a return (−) electrode may be positioned in a spaced apart relationship on the shaft of an electrosurgical probe such that electrosurgical currents are passed along, or parallel to the shaft.

Alternatively, a first probe may function as an active (+) electrode and a second probe may function as a return (−) electrode. The first and second probes are positioned in a spaced apart relationship relative to each other such that electrosurgical currents are passed between the active (+) and return (−) electrodes resulting in the ablation of tissue positioned between the two probes. As such, the ablation region is defined by the spacing between the active (+) and return (−) electrodes and heating of tissue is typically confined therebetween. During ablation, current pathways in tissue between the active (+) and return (−) electrode produces localized heating between the two probes.

Radio frequency energy in a microwave frequency range may be delivered to a targeted tissue by a microwave energy delivery device with a microwave antenna on the distal tip. The antenna of the microwave energy delivery device, when provided with a microwave energy signal, generates electromagnetic fields in the adjacent tissue without the generation of electrosurgical currents between an active electrode and a return electrode as discussed hereinabove.

While the ablation region produced by ablation probes is defined by the current path between the electrodes, the ablation region (shape and area) produced by a microwave energy delivery device is defined by the type of antenna, the frequency of the microwave energy signal and the power level of the microwave energy signal. For example, an ablation region generated by a microwave energy delivery device may be symmetric about the tip and shaft of the microwave energy delivery device, directed to only one side of the shaft or if the antenna is unchoked, the ablation region may include a "tail" portion that extends proximally up the elongated shaft of the microwave energy delivery device.

Unlike radio frequency probes, microwave energy delivery devices need not be configured to interact with each other. In fact, microwave energy delivery devices typically do not interact since any interaction would be due to the intermingling of the electromagnetic fields generated by the two devices i.e., the two devices placed in close proximity may result in the overlapping of electromagnetic fields generated by each microwave energy delivery device. The overlapping electromagnetic fields may result in unpredictable results as the electromagnetic fields may cancel each other (resulting in no heating), the electromagnetic fields may, combine (resulting in the generation of pockets of extremely high current densities) or any combination thereof. As such, controlling the interaction between microwave energy delivery devices becomes even more complicated when the surgical procedures requires the insertion of a plurality of microwave energy delivery devices.

The unpredictable nature of the overlapping electromagnetic fields can be overcome by precisely placing the microwave energy delivery devices in a target tissue. The present disclosure describes apparatuses, systems and methods for precise placement of microwave energy delivery devices in a surgical procedure.

SUMMARY

The present disclosure describes an apparatuses, systems and methods for precise placement of microwave energy deliver devices in a surgical procedure. The microwave energy delivery device positioner includes a body, a plurality of legs operably coupled to the body and a plurality of ribs connected to the body. The body includes a body facing surface and a plurality of device positioner apertures defined therein. The device positioner apertures are configured to receive a microwave energy delivery device therethrough. The plurality of legs includes one or more feet extending beyond the patient facing surface of the body with the distal end of the feet being configured to contact patient tissue and elevate the patient facing surface of the body such that the patient facing surface is spaced away from patient tissue. The plurality of ribs form at least one air flow aperture.

The plurality of device positioner apertures further includes a first set of device positioner apertures defined therein and a second set of device positioner apertures defined therein. The first and second sets of device positioner apertures may include three apertures having radial centers equally spaced relative to one another. At least one radial center of the second set of device positioner apertures may be positioned about midway between two of the first set of device positioner apertures.

In one embodiment the plurality of legs may be substantially equal in length and may elevate the tissue facing surface of the body at least ½ inch relative to body tissue. The plurality of ribs may be configured to provide structural rigidity and may form at least three air flow, apertures defined therefrom.

In another embodiment the plurality of device positioner apertures formed by the body may be substantially parallel such that the microwave energy delivery devices inserted through the plurality of device positioner apertures are maintained in a substantially parallel orientation.

The present disclosure also discloses an electrosurgical ablation system including a microwave energy source, a microwave positioner of the present disclosure and a plurality of tissue penetrating microwave energy delivery devices with a microwave antenna at the distal tip thereof, the antenna configured to receive a microwave energy signal from the microwave energy source and to radiate microwave energy therefrom. The microwave positioner includes a body, defining a plurality of device positioner apertures and a patient facing surface, a plurality of legs operably coupled to the body and a plurality of ribs connected to the body and forming at least one air flow apertures. The legs include one or more feet extending beyond the patient facing surface of the body, the feet being configured to contact patient tissue. The device positioner apertures formed by the body are configured to receive tissue penetrating microwave devices therethrough. The feet and legs elevate the patient facing surface of the body such that the patient facing surface is spaced away from patient tissue.

In one embodiment the plurality of device positioner apertures are configured to guide the tissue penetrating microwave devices. The plurality of device positioner apertures may further include a first and a second set of device positioner apertures defined therein. The first set of device positioner apertures may include three apertures having radial centers equally spaced relative to one another. The second set of device positioner apertures may include radial centers equally spaced relative to one another with at least one radial center being positioned about midway between two of the first set of device positioner apertures.

In another embodiment the plurality of legs may include three feet substantially equal in length that elevate the tissue facing surface of the body at least ½ inch relative to body tissue.

The present disclosure also includes a method for positioning a plurality of tissue penetrating microwave energy delivery devices, the method including the steps of: positioning a microwave positioner on patient tissue adjacent a target tissue; inserting a first tissue penetrating microwave energy delivery device, including a shaft with an antenna on the distal end thereof, through a first device positioning aperture formed in the body of the microwave positioner, the first device positioning aperture configured to guide the first tissue penetrating microwave energy delivery device; advancing the antenna of the first tissue penetrating microwave energy delivery device to a target tissue; inserting a subsequent tissue penetrating microwave energy delivery device through a second device positioning aperture formed in the body of the microwave positioner; and advancing the subsequent tissue penetrating microwave energy delivery device antenna to a target tissue, wherein the elongated shaft of the first tissue penetrating microwave energy delivery device is maintained in a substantially parallel orientation to the elongated shaft of the subsequent tissue penetrating microwave energy delivery device.

In one embodiment the microwave positioner includes a body having a plurality of device positioner apertures defined therein. The body includes a patient facing surface, a plurality of legs operably coupled to the body including one or more feet extending beyond the patient facing surface of the body the distal ends of the feet are configured to contact patient tissue. A plurality of ribs connect to the body and form at least one air flow aperture. The plurality of device positioner apertures formed by the body are configured to receive a microwave energy delivery, device therethrough and the plurality of legs elevate the patient facing surface of the body such that the patient facing surface is spaced away from patient tissue.

The method may further include the step of delivering microwave energy to the target tissue. The at least one air flow aperture may facilitate cooling of the first tissue penetrating microwave energy delivery device.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
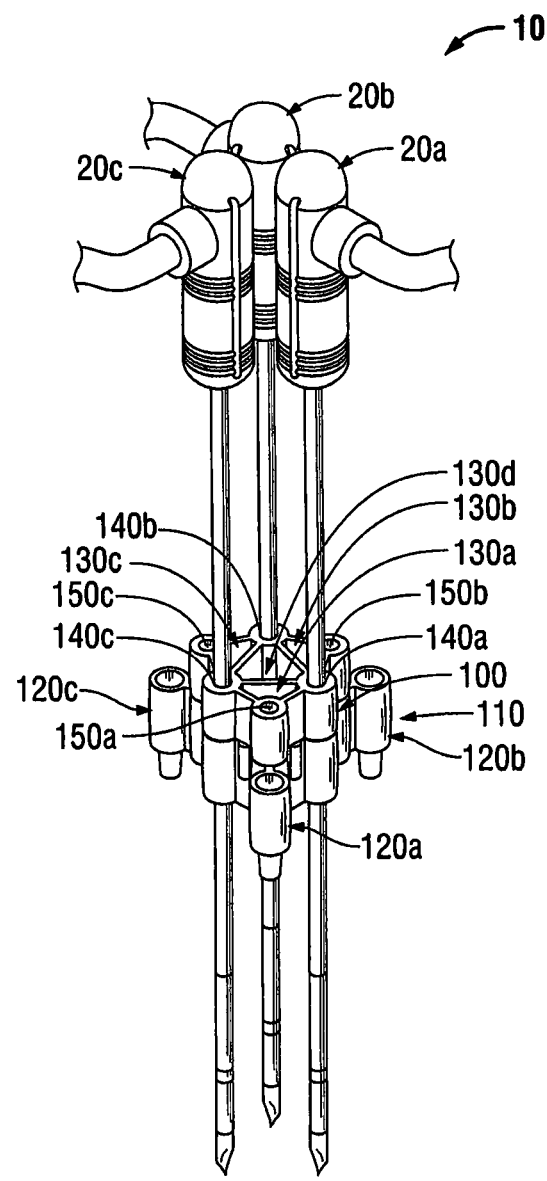
FIG. 1 is a perspective view of a microwave positioner, in accordance with an embodiment of the present disclosure, positioning three microwave energy delivery devices in a first configuration.

Particular embodiments of the present disclosure will be described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user. In addition, although the following description describes the present invention with respect to a microwave antenna application, the present invention may also be applicable to other energy-based applications, such as RF ablation probes, cryo probes, and the like.

FIG. 1 shows a perspective view of a microwave positioner 100 in accordance with the present disclosure. Body 110 of the microwave positioner 100 forms a plurality of legs 120a-120c and a plurality of apertures 140a-140c, 150a-150c and 130a-130d defined therein, the plurality of apertures extending longitudinally through the body. The microwave positioner 100 includes three sets of apertures, namely a plurality of first position device apertures 140a-140c, a plurality of second position device apertures 150a-150c and a plurality of airflow apertures 130a-130d.

Legs 120a-120c position the microwave positioner 100 on the patient. As better illustrated in FIG. 2, the underside of each leg includes a foot 121a-121c that makes contact with patient tissue and aids in securing the microwave positioner 100 to the patient. Each foot 121a-121c may include an adhesive coating, non-skid cover, or a non-slip surface, or any other suitable surface or coating that aids in securing the microwave positioner 100 to the patient. It is envisioned that microwave positioner 100 may include three or more legs to secure the microwave positioner 100 to the patient.

Figure 2:
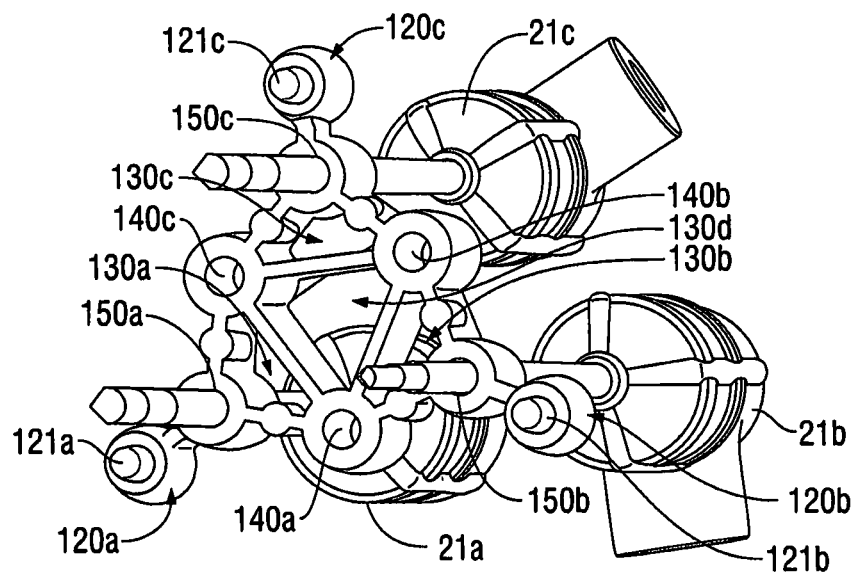
FIG. 2 is a perspective view from the underside of the microwave positioner of FIG. 1, illustrating airflow passageways through the microwave positioner and positioning three microwave energy delivery devices in a second configuration.

The first position device apertures 140a-140c and the second position device apertures 150a-150c form a channel configured to guide at least a portion of the microwave energy deliver), devices 20a-20c. As illustrated in FIG. 1, the first position device apertures 140a-140c position the microwave energy delivery devices 20a-20c in close relationship with respect to each other. As illustrated in FIG. 2, the second position device apertures 150a-150c position the microwave energy delivery devices 21a-21c in a spaced apart relationship as compared to the spacing of the microwave energy delivery devices 20a-20c when inserted through the first position device apertures 140a-140c.

Microwave positioner 100 is configured to provide a plurality of microwave energy delivery device orientations with varying spacing between each microwave energy delivery device. The spacing between the position apertures is further illustrated in FIG. 3. The portion of the body 110 that forms the first position device apertures 140a-140c positions the radial centers of the three first position device apertures 140a-140c such that the three centers form the corners of a first equilateral triangle, the sides of which are about equal to a distance D1. The portion of the body 10 that forms the second position device apertures 150a-150c positions the radial centers of the three second position device apertures 150a-150c such that the three radial centers form the corners of a second equilateral triangle, the sides of which are about equal to a distance D2. The first and second equilateral triangles are similarly arranged to a so-called "Sierpinski Triangle" where the first equilateral triangle is nested within the second equilateral triangle and D1 is necessarily less than D2.

Interior ribs 111-113 of the body 110 form the sides of the first equilateral triangle and provide structural strength to the interior of the microwave positioner 100. Interior ribs 111-113 also form the center airflow aperture 130d.

Exterior ribs 114-119 form the sides of the second equilateral triangle and provide structural strength to the exterior of the microwave positioner 100. Outer airflow apertures 130a, 130b, 130c are formed between one of the interior ribs 111-113 and at least two of the exterior ribs 114-119. Ribs 111-119 may also include rib stiffeners, as illustrated on exterior ribs 114-119, to provide additional strength, to prevent deflection and/or to prevent the microwave positioner 100 from changing form. Ribs 111-119 are configured to maintain the structure of the microwave positioner.

Figure 4:
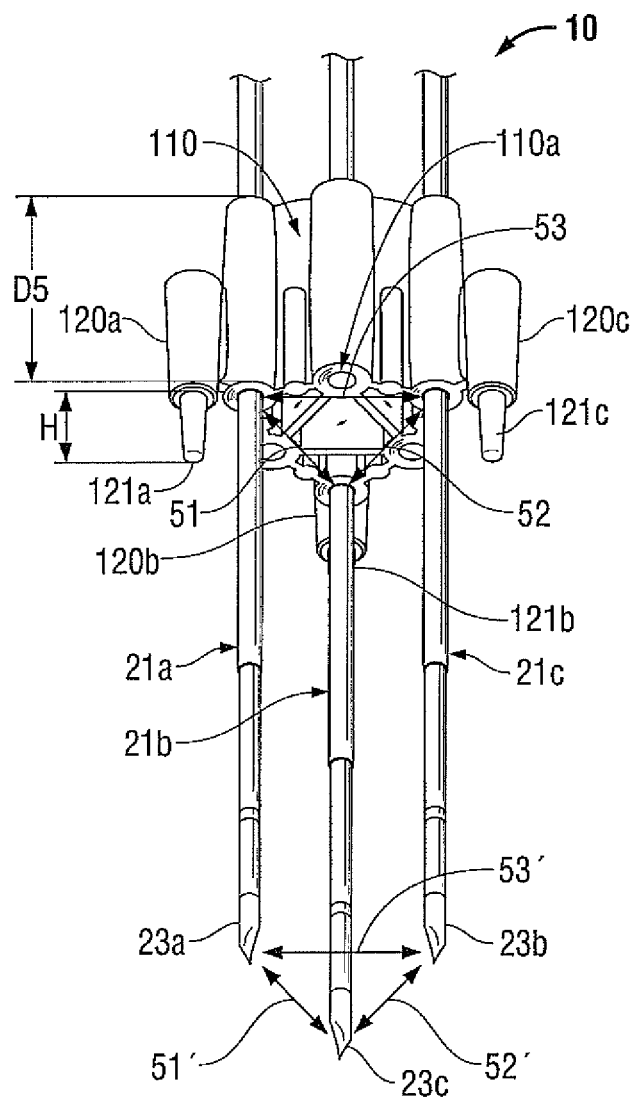
FIG. 4 is a perspective view of the microwave positioner of FIG. 1 and the distal antenna portions of the microwave energy delivery devices.

Each leg 120a-120c connects to the portion of the body that forms the second position device apertures 150a-150c. The radial centers of the legs 120a-120c form a third equilateral triangle with the distance between each leg equal to D3, wherein distance D3 is greater than distance D2. As best illustrated in FIG. 4, feet 121a-121c extend from each leg 120a-120c, respectively, thereby extending the feet below the body lower surface 110a of the body 110 and the leg 120a-120c. Each foot 121a-121c extends beyond the body lower surface 110a a distance H such that the body 110 of the microwave positioner 100 is spaced away from patient tissue. In one embodiment, feet 121a-121c space the body lower surface 110a at least ½ inch away from patient tissue. In another embodiment the height H of the feet are not equal.

Figure 3:
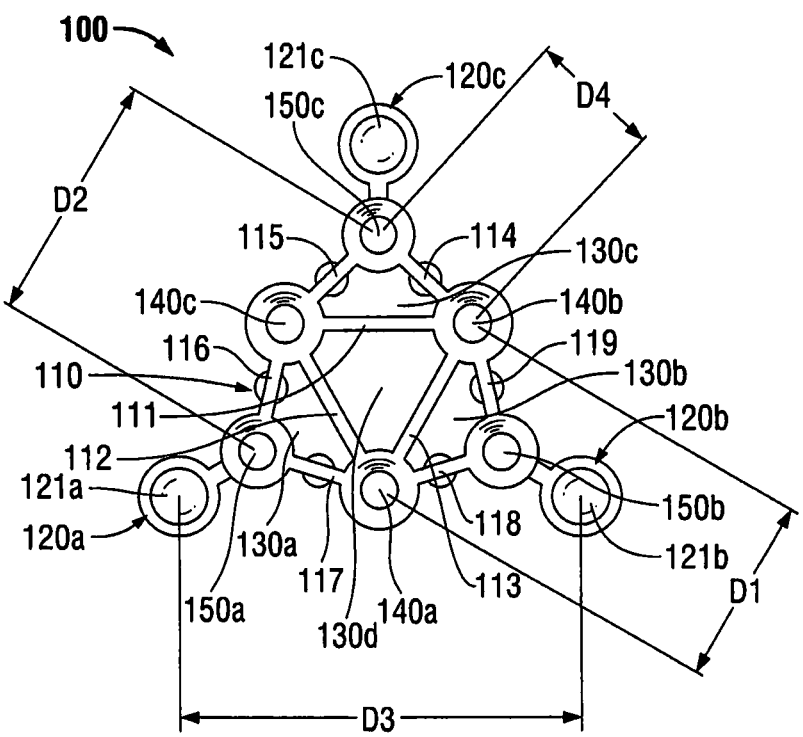
FIG. 3 is a top view of the microwave positioner of FIG. 1.

As illustrated in FIGS. 2 and 3, center airflow aperture 130d and outer airflow apertures 130a-130c are configured to allow heat (generated at the surface of the patient tissue) to dissipate through the microwave positioner 100a. The distal end of the feet 121a-121c contact patient tissue (not shown) and elevate the microwave positioner 10 a distance H (See FIG. 4) above patient tissue, thereby allowing air to freely flow between the lower surface 110a of the body 110, through the center airflow aperture 130d and the outer airflow apertures 130a-130c. Thermal energy generated at the surface of the patient tissue dissipates through one of the center airflow aperture 130d and the outer airflow apertures 130a-130c. Body 110 of the microwave positioner 10 may be formed from a light weight material resistance to thermal heating.

A microwave ablation procedure using a microwave positioner of the present disclosure may require the use of a plurality, of microwave energy delivery devices. In use, each of the microwave energy delivery devices is inserted through one of the apertures 140a-140c, 150a-150c formed in the body 110 of the microwave positioner 100. The microwave ablation procedure may require the use of any number and any combination of apertures 140a-140c, 150a-150c. Apertures that are not used for the insertion of microwave energy delivery devices may be used for the placement of other probes or sensors, such as, for example, one or more temperature probes or sensors.

One particular microwave ablation procedure may include the use of the three first position device apertures 140a-140c as illustrated in FIG. 1. Microwave energy delivery devices 20a, 20b, 20c are inserted in each of the first positioner device apertures 140a-140c, respectively. One or more of the second positioner device apertures 150a-150c may be used for positioning a temperature sensor or other suitable sensing device. As illustrated in FIG. 3, each of the second positioner device apertures 150a-150c is positioned a distance D4 from at least two of the first position device apertures.

With continued reference to FIG. 3, the distances D1, D2, D3 between the various apertures 140a-140c, 150a-150c formed in the body 110 of the microwave positioner 100 and the dimensions of the apertures 140c-140a, 150a-150c may vary. Distances and dimensions may be adjusted for the type of microwave energy delivery devices used in the procedure, the amount of energy delivered to the target tissue from the microwave energy delivery, devices, the number of microwave energy delivery devices required for the procedure, the number and type of sensors used to measure a tissue parameter, and specific location on the patient where the microwave positioner may be placed. In addition, there may be advantages to the have the ability to change the shape or configuration of the microwave positioner 100. Cancerous growths may be irregular in size and shape. Thus, by being able to change the shape of the microwave positioner 100, a surgeon may have more control and precision in treating the growth. For example, the surgeon may need to achieve a radius or some other shape to capture the circumference of the growth. This may be accomplished by having ribs 111-119 adjustable by having a telescopic configuration or being flexible or malleable.

Another microwave ablation procedure may require the use of three second position device apertures 150a-150c as illustrated in FIGS. 2 and 4. One or more of the first positioner device apertures 140a-140c may be used for positioning a temperature sensor or other suitable sensing device.

As illustrated in FIG. 4, the portion of the body 110 forming the first position device apertures 140a-140c and the second position device apertures 150a-150c includes a height equal to D5. As such, each apertures 140a-140c, 150a-150c, formed in the body also includes a length of D5. The aperture length D5 is sufficiently long to guide the microwave energy delivery devices 21a-21c such that the distal ends of the devices are positioned in a desirable spaced apart relationship relative to each other such that the spacing of the distal tips 51', 52' and 53' are desirably spaced.

In one embodiment, the apertures 140a-140c, 150a-150c formed in the body 110 are substantially parallel to each other. The apertures 140a-140c, 150a-150c are configured to guide the microwave energy delivery devices 21a-21c such that the elongated shafts 22a-22c when inserted in the microwave positioner 10 are maintained in a substantially parallel orientation to each other. As such, the spacing S1', S2' and S3' between the distal tips 23a-23c of each of the microwave energy delivery devices 21a-21c is substantially equal.

Microwave spacer may be formed with specific dimensions and tight tolerances in order to provide desirable spacing between apertures. The internal aperture dimensions may also include specific dimensions and tight tolerances in order to provide adequate guidance of the microwave energy delivery devices during insertion. For example, the microwave spacer may be formed by any suitable process, such as injection molding or casting. In addition, any suitable material may be utilized, such as plastic, ceramic, composite material, etc.

In another embodiment, the apertures 140a-140c, 150a-150c formed in the body 110 are not substantially parallel to each other. Apertures 140a-140c, 150a-150c may angle slightly inward such that the spacing 51', 52' and 53' between the distal tips 23a-23c is less than the aperture spacing D1, D2, respectively (D1 and D2, as illustrated in FIG. 2 e.g., the spacing between the radial centers of the apertures 140a-140c, 150a-150c).

The portion of the body 110 that forms the first position device apertures 140a-140c positions the radial centers of the three first position device apertures 140a-140c such that the three centers approximately form the corners of a first equilateral triangle, the sides of which are about equal to a distance D1. The portion of the body 110 that forms the second position device apertures 150a-150c positions the radial centers of the three second position device apertures 150a-150c such that the three centers approximately form the corners of a second equilateral triangle, the sides of which are about equal to a distance D2. The first and second equilateral triangles are similarly arrange in a "Sierpinski Triangle" where the first equilateral triangle is nested within the second equilateral triangle and D1 is less than D2.

The embodiments described herein should not be limited to the figures and specific geometries illustrated herein as any suitable geometry and dimensioning may be used to construct a microwave positioner of the present disclosure. For example, a square-shaped microwave positioner may include four legs (one on each corner) configured to contact tissue, and a body that forms a first set of device positioning apertures (with a plurality of apertures) and a second set of device positioning apertures (with a plurality of apertures). The first and/or the second set of device positioning apertures formed by the body are nested within the square formed by the four legs. The body further includes a suitable number of ribs that connect the legs and the portion of the body that forms the apertures. The ribs also provide structural strength to the microwave positioner and form a plurality of airflow apertures through the body.

Figure 5:
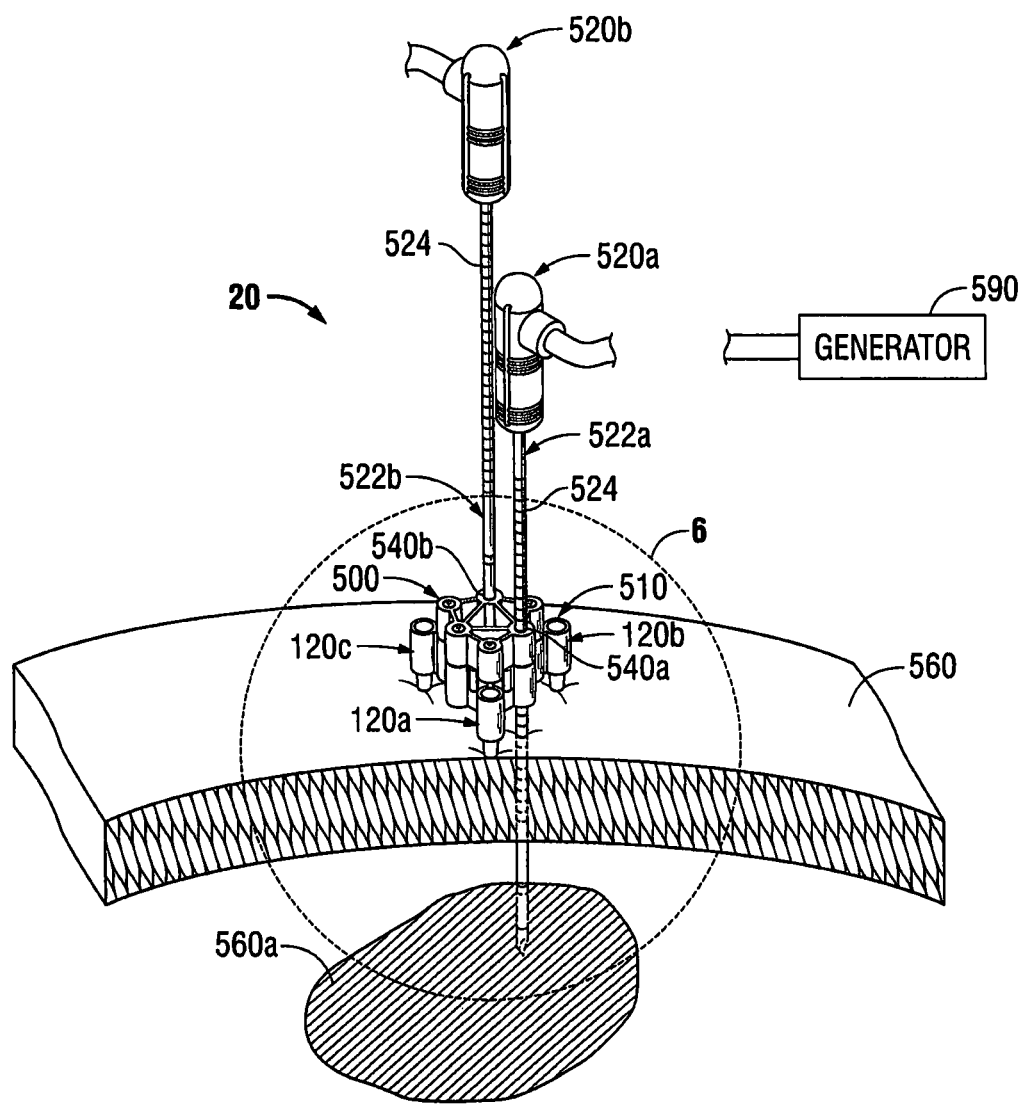
FIG. 5 is an illustration of a microwave energy delivery system including a microwave positioner of the present disclosure.
Figure 6:
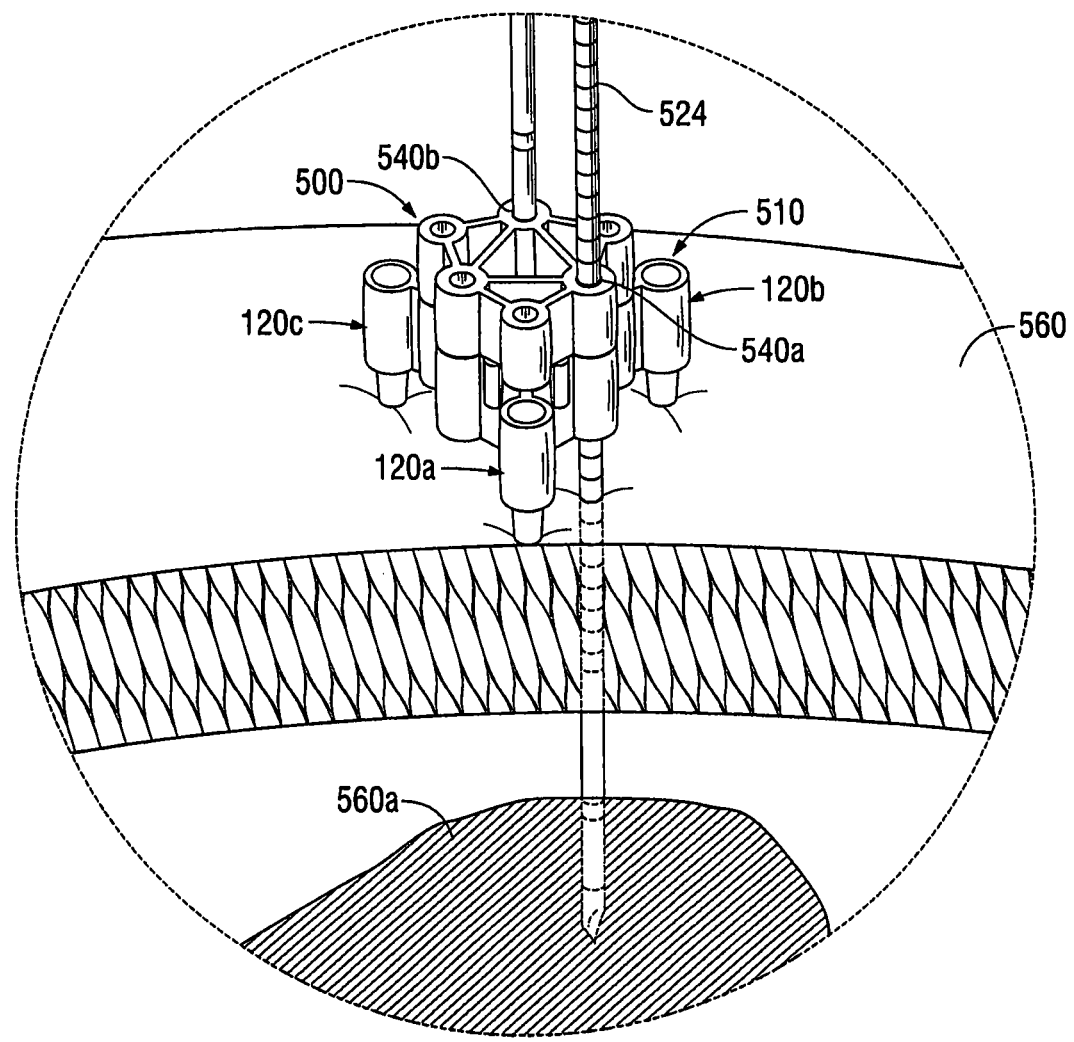
FIG. 6 is a perspective view of a portion of the microwave energy delivery system of FIG. 5.

FIGS. 5 and 6 illustrate a microwave energy delivery system 20 including a microwave positioner 500, as described and illustrated in the present disclosure, and a plurality of microwave energy delivery devices 520a, 520b. The microwave energy delivery devices 520a, 520b connect to a microwave generator 590 and are configured to deliver microwave energy to a target tissue 560a.

In use, the microwave positioner 500 is placed on the patient tissue 560 proximal to the target tissue 560a. A first microwave energy delivery device 520a is inserted through a first selected aperture 540a formed in the body 510 of the microwave positioner 500. The first selected aperture 540a guides the first microwave energy delivery device 520a while being advanced to the patient tissue 560 and inserted to the target tissue 560a. Shaft 522a, 522b of the microwave energy delivery devices 520a, 520b may include a plurality of position indicating markers 524 that indicate the depth of insertion.

A second microwave energy delivery device 520b is inserted through a second selected aperture 540b formed in the body of the 510 of the microwave positioner 500. Additional microwave energy deliver), devices and/or sensing devices may be inserted through additionally selected apertures.

A method for placing a plurality of microwave energy delivery devices and ablating tissue includes the steps of: placing the microwave positioner described in the present disclosure on a portion of patient's tissue adjacent a target tissue; inserting two or more microwave energy delivery devices through apertures formed in the body of the microwave positioner into the target tissue; connecting the two or more microwave energy delivery devices to a microwave energy source; ablating the target tissue by delivering microwave energy through the microwave energy delivery devices and cooling the patient's tissue by providing airflow through a plurality of airflow apertures formed through the microwave positioner.

Two or more microwave positioners may be configured to connect and form an interlocking microwave spacer. Spacers may be daisy-chained together or may be grouped together in a specific pattern. The connection between microwave positioners may be accomplished by connection points formed on the microwave positioners or may be accomplished by utilizing a linking connector that is configured to link the two or more microwave positioners. In one embodiment, connecting the two or more microwave positioners positions a set of apertures to form a resection line.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An energy delivery device positioner, comprising:
 a body having a plurality of device positioner apertures defined therein, the body including a patient facing surface;
 a plurality of legs coupled to the body, including at least one foot extending beyond the patient facing surface of the body, a distal end of the at least one foot configured to contact patient tissue;
 a plurality of ribs forming the body and forming at least one air flow aperture through the body and between two or more of the plurality of ribs; and
 wherein the plurality of device positioner apertures are configured to receive an energy delivery device therethrough and wherein the at least one foot elevates the patient facing surface of the body away from patient tissue.

2. The positioner according to claim 1, wherein the plurality of device positioner apertures further includes a first set of three device positioner apertures having radial centers equally spaced relative to one another.

3. The positioner according to claim 2, wherein the plurality of device positioner apertures further includes a second set of three device positioner apertures, the second set of three device positioner apertures being different than the first set of three device positioner apertures, the second set of three device positioner apertures having radial centers equally spaced relative to one another.

4. The positioner according to claim 3, wherein at least one aperture of the second set of three device positioner apertures is positioned about midways between two apertures of the first set of three device positioner apertures.

5. The positioner according to claim 1, wherein the plurality of legs includes three legs substantially equal in length.

6. The positioner according to claim 5, wherein the plurality of legs elevate the tissue facing surface of the body at least 0.5 inches relative to patient tissue.

7. The positioner according to claim 1, wherein the plurality of ribs are configured to provide structural rigidity.

8. The positioner according to claim 1, wherein the at least one air flow aperture includes at least three air flow apertures through the body, wherein each of the at least three air flow apertures is formed between the two or more of the plurality of ribs.

9. The positioner according to claim 1, wherein the plurality of device positioner apertures formed by the body are substantially parallel.

10. The system according to claim 1, wherein the plurality of ribs includes at least three ribs.

* * * * *